(12) United States Patent
Tai et al.

(10) Patent No.: US 7,530,259 B2
(45) Date of Patent: May 12, 2009

(54) ON-CHIP TEMPERATURE CONTROLLED LIQUID CHROMATOGRAPHY METHODS AND DEVICES

(75) Inventors: Yu-Chong Tai, Pasadena, CA (US); Jun Xie, Pasadena, CA (US); Chi-yuan Shih, Pasadena, CA (US); Qing He, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/059,625

(22) Filed: Feb. 17, 2005

(65) Prior Publication Data

US 2005/0274174 A1 Dec. 15, 2005

Related U.S. Application Data

(60) Provisional application No. 60/545,727, filed on Feb. 17, 2004.

(51) Int. Cl.
*G01N 1/00* (2006.01)
*G01N 30/00* (2006.01)

(52) U.S. Cl. ............... 73/61.57; 73/61.52; 73/61.58

(58) Field of Classification Search ........... 73/61.52, 73/61.53, 61.57, 61.58
See application file for complete search history.

(56) References Cited

U.S. PATENT DOCUMENTS

| | | | |
|---|---|---|---|
| 5,135,549 A * | 8/1992 | Phillips et al. | 95/8 |
| 6,526,823 B2 | 3/2003 | Tai et al. | |
| 6,663,697 B1 | 12/2003 | Kottenstette et al. | |
| 6,666,907 B1 | 12/2003 | Manginell et al. | |
| 6,838,640 B2 | 1/2005 | Wise et al. | |
| 2003/0228411 A1 | 12/2003 | Tai et al. | |
| 2004/0188648 A1 | 9/2004 | Tai et al. | |
| 2005/0051489 A1 | 3/2005 | Tai et al. | |

FOREIGN PATENT DOCUMENTS

EP          0 770 871 A          5/1997

OTHER PUBLICATIONS

Andersen et al., "Characterization of complex mixtures of polyglycerol fatty acid esters using temperature and solvent gradients in packed capillary LC," Journal of Separation Science, vol. 26, pp. 1133-1140, (2003).

Boyd et al., "Trace-Level Amino Acid Analysis by Capillary Liquid Chromatography and Application to in Vivo Microdialysis Sampling with 10-s Temporal Resolution," Analytical Chemistry, vol. 72, No. 4, pp. 865-871, (Feb. 15, 2000).

(Continued)

*Primary Examiner*—Daniel S Larkin
(74) *Attorney, Agent, or Firm*—Foley & Lardner LLP

(57) ABSTRACT

An apparatus for liquid chromatography comprises a liquid chromatography separation column on a substrate, wherein the separation column is coupled to a heater on the substrate. A chip-based temperature controlled liquid chromatography device comprises a substrate, a thermal isolation zone, and a separation column thermally isolated from the substrate by the thermal isolation zone. An apparatus for chip-based liquid chromatography comprising a cooling device is provided. A temperature gradient liquid chromatography system comprises a chip-based temperature controlled liquid chromatography device, a fluidic coupling, and an electrical interface. Methods of making and methods of using of chip-based temperature gradient liquid chromatography devices are also provided.

16 Claims, 17 Drawing Sheets
(17 of 17 Drawing Sheet(s) Filed in Color)

OTHER PUBLICATIONS

Chang et al., "Polymer characterization by non-size exclusion chromatography: Temperature gradient interaction chromatography," American Laboratory, pp. 39-41, (Jul. 2002).

Greibrokk, "LC Columns: LC Might be a Mistake," Analytical Chemistry, pp. 375A-378A, (Jul. 1, 2002).

Greibrokk, et al., "Temperature programming in liquid chromatography," Journal of Separation Science, vol. 24, pp. 899-909, (2001).

He et al., "Ion Liquid Chromatography On-A-Chip with Beads-Packed Parylene Column," IEEE MEMS, (2004).

Lee et al., "Temperature gradient interaction chromatography of low molecular weight polystyrene," Polymer, vol. 40, pp. 7227-7231, (1999).

Meng et al., "A Parylene MEMS Flow Sensing Array," 12th International Conference on Solid State Sensors, Actuators, and Microsystems, Transducers, pp. 686-689, (Jun. 8-12, 2003).

Meyer, *Practical High-Performance Liquid Chromatography*, John Wiley & Sons, England, pp. 310-311, (1999).

Molander et al., "The impact of column inner diameter on chromatographic performance in temperature gradient liquid chromatography,." The Analyst, vol. 12B, No. 11, pp. 1341-1345, (2003).

Panagiotopoulos et al., "Sub-ambient temperature effects on the seperation of monosaccharides by high-performance anion exchange chromatography with pulse amperometric detection Application to marine chemistry," Journal of Chromatography A, vol. 902, pp. 13-22, (2001).

Shackelford, *Introduction to Material Science for Engineers, Fourth Edition*, Prentice Hall, USA, pp. 327-328, (1996).

Shin et al., "On-Chip Temperature Gradient Liquid Chromatography," IEEE MEMS, pp. 782-785, (2005).

International Search Report, PCT/US05/05219 (Jun. 14, 2005).

Carlier et al., "Integrated microfabricated systems including a purification module and an on-chip nano electrospray ionization interface for biological analysis," Journal of Chromatography A, 1071, 2005, pp. 213-222.

Chervet et al., "Instrumental Requirements for Nanoscale Liquid Chromatography," Anal. Chem., 1996, vol. 68, pp. 1507-1512.

Deal et al., "General Relationship for the thermal Oxidation of Silicon," J. Appl. Physics, Dec. 1965, vol. 36, No. 12, pp. 3770-3778.

Ericson et al., "Electroosmisos- and Pressure-Driven Chromatography in Chips Using Continuous Beds," Anal. Chem. 2000, vol. 72, pp. 81-87.

Garcia et al., "Direct Determination of Carbohydrates Amino Acids, and Antibiotics by Microchip Electrophoresis with Pulsed Amperometric Detection," Anal. Chem., 2003, vol. 75, pp. 4778-4783.

Greibrokk et al., "High-temperature liquid chromatography," Journal of Chromatography A, 1000 (2003), pp. 743-755.

Harris, C.M., "Shrinking the LC Landscape," Anal Che.m, 2003, vol. 75, pp. 64A-69A.

He et al., "Fabrication of Nanocolumns for Liquid Chromatography," Anal. Chem., 1998, vol. 70, pp. 3790-3797.

Hirata et al., "Temperature-programmed reversed-phase liquid chromatography with packed fused-silica columns," Journal of Chromatography, 267 (1983), pp. 125-131.

Houdiere et al., "Combination of Column Temperature Gradient and Mobile Phase Flow Gradient in Microcolumn and Capillary Column High-Performance Liquid Chromatography," Anal. Chem., 1997, vol. 69, pp. 2589-2593.

Jinno, Kiyokatsu, "Temperature-Controlled High-Speed Microcolumn Liquid Chromatography," Anal. Chem. 1985, vol. 57, pp. 574-576.

Kricka et al., "Microchip PCR," Anal. Bioanal. Chem., 2003, vol. 377, pp. 820-825.

LaCourse, William R., "Column Liquid Chromatography: Equipment and Instrumentation," Anal. Chem., 2002, vol. 74, pp. 2813-2832.

Liger et al., "Robust parylene-to-silicon mechanical anchoring," Proceedings of the IEEE International Conference on MicroElectroMechanical Systems (MEMS 2003), Kyoto, Japan, 2003, pp. 602-605.

Manz et al., "Design of an Open-tubular Column Liquid Chromatograph Using Silicon Chip Technology," Sensors and Actuators, B1, 1990, pp. 249-255.

McEnery et al., "Liquid chromatography on-chip: progression towards a μ-total analysis system," Analyst, 2000, vol. 125, pp. 25-27.

Murrihy et al., "Ion chromatography on-chip," Journal of Chromatography A, 924 (2001), pp. 233-238.

Shih et al., "Yield strength of thin-film parylene-C," Microsystem Technologies 10 (2004), pp. 407-411.

Strain, Harold H., "Conditions Affecting the Sequence of Organic Compounds in Tswett Adsorption Columns," Ind. Eng. Chem. Anal. Ed. 18, 1946, pp. 605-609.

Sun et al., "A heater-integrated transparent microchannel chip for continous-flow PCR," Sensors and Actuators B, 84 (2002), pp. 283-289.

Szumski et al., "State of the Art in Miniaturized Separation Techniques," Critical Reviews in Analytical Chemistry, 2002, vol. 32, No. 1, pp. 1-46.

Trones et al., "High Temperature Liquid Chromatography on Packed Capillary Columns with Nonaqueous Mobile Phases," J. Microcolumn Separations, 1995, vol. 7, No. 5, pp. 505-512.

Vervoort et al., "Importance and Reduction of the Sidewall-Induced Band-Broadening Effect in Pressure-Driven Microfabricated Columns," Anal. Chem. 2004, vol. 76, pp. 4501-4507.

Wang et al., "Micromachined Separation chips with a Precolumn Reactor and End-Column Electrochemical Detector," Anal. Chem., 2000, vol. 72, pp. 5774-5778.

Wolcott et al., "Control of column temperature in reversed-phase liquid chromatography," Journal of Chromatography A, 869 (2000), pp. 211-230.

Xie et al., "An Electrical Pumping System for On-Chip Gradient Generation," Anal. Chem., 2004, vol. 76, pp. 3756-3763.

Xie et al., "An Integrated LC-ESI chip with electrochemical-based gradient generation," Proceedings of the 17th IEEE International Conference on MicroElectroMechanical Systems (MEMS 2004), Maastricht, The Netherlands, 2004, pp. 334-337.

Yin et al., "Microfluidic Chip for Peptide Analysis with an Integrated HPLC Column, Sample Enrichment Column, and Nanoelectrospray Tip," Anal. Chem., 2005, vol. 77, pp. 527-533.

European Search Report, Appl. No. 05723290.2 (PCT/US2005/005219), 4 pages (Sep. 7, 2007).

* cited by examiner

FIGURE 5.

Grow oxide, pattern front oxide, deposit Pt/Ti/Au, pattern Au, pattern Pt/Ti, pattern backside oxide, backside DRIE

Deposit and pattern 1st parylene, deposit and pattern photoresist, front side DRIE

Deposit and pattern 2nd parylene, backside DRIE to open through holes, front side $XeF_2$ etch

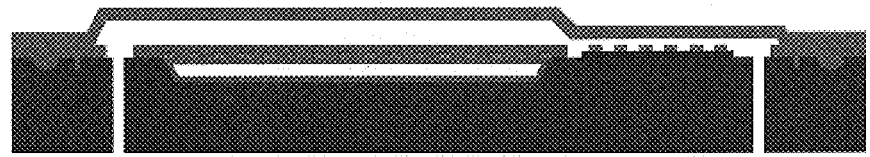

Deposit 3rd parylene, dicing, release photoresist, pattern parylene with shadow masking Pt/Ti  Parylene  Silicon  Oxide  Photoresist 1st, 2nd, 3rd parylene layer

FIGURE 8.
Grow oxide, coat and pattern PR, deposit Pt/Ti/Au, liftoff, pattern Au, pattern front side oxide, pattern backside oxide, backside DRIE
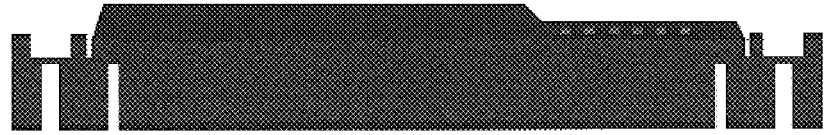
Deposit and pattern photoresist, front side DRIE
Deposit and pattern parylene
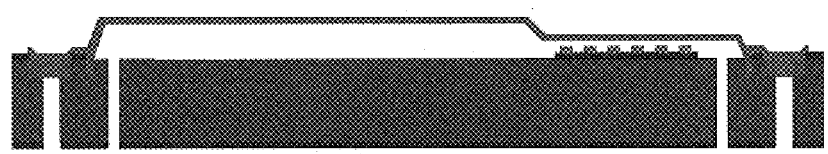
Backside DRIE, dicing, release photoresist,
▒ Pt/Ti  ▒ Parylene  ▒ Silicon  ▒ Oxide  ▒ Photoresist

ON-CHIP TEMPERATURE CONTROLLED LIQUID CHROMATOGRAPHY METHODS AND DEVICES

CROSS-REFERENCE TO RELATED PATENT APPLICATIONS

This application claims priority to U.S. Provisional Application No. 60/545,727 filed Feb. 17, 2004 (CalTech Ref. No.: CIT-4046P) "On-Chip Temperature Controlled Liquid Chromatography Methods and Devices" which is hereby incorporated by reference in its entirety.

STATEMENT OF GOVERNMENT SUPPORT

Notice is hereby provided that certain aspects of the invention have been funded, in part, by Center for Neuromorphic Systems Engineering (CNSE) NSF Contract #EEC-9402726, and the federal government may have certain rights in the invention.

BACKGROUND

Liquid chromatography (LC) is a powerful analytical tool for molecular separation. Temperature variation can be an important parameter in liquid chromatography (see e.g. T. Greibrokk, T. Andersen, *Journal of Separation Science*, 24, 899-909, 2001; T. Greibrokk, *Analytical Chemistry*, 74(13), 374A-378A, 2002). Temperature can affect several physical parameters in LC such as retention factor, analyte solubility, diffusivity, and mobile phase viscosity. However, temperature control can be slow and difficult to implement due to radial temperature gradients associated with the large sizes of traditional chromatography columns.

The recent trend toward miniaturization of chromatography columns has stimulated research into temperature control (V. R. Meyer, "Practical High-Performance Liquid Chromatography", John Wiley & Sons, 1999, 310-311). For example, temperature controlled separation columns were microfabricated for gas chromatography (U.S. Pat. No. 6,666,907 to Manginell et. al. issued Dec. 23, 2003, U.S. Pat. No. 6,663,697 to Kottenstette et. al. issued Dec. 16, 2003, and U.S. Pat. No. 6,838,640 to Wise et. al. issued Jan. 4, 2005). Yet, it is highly desirable to develop an on-chip, temperature controlled system for liquid chromatography. LC provides greater engineering challenges in view of the high pressures. Moreover, it is a challenge to generate and control temperature gradients on chips, particularly in view of the high thermal conductivity of silicon, and a need exists for better thermal management systems including better heating and cooling systems. Also, a need exists for better integrated systems, wherein device components are fabricated on a common substrate using sequential processing steps.

SUMMARY

This invention in its various embodiments relates to chromatography in general and to high pressure chromatography and liquid chromatography in particular. Provided is an on-chip temperature controlled liquid chromatography system, methods of making the system, and methods of using the system.

One embodiment of the invention is an apparatus for liquid chromatography comprising a liquid chromatography separation column on a substrate, wherein the column is coupled to a heater on the substrate. The heater can control column temperature during separation. Applied current to the heater can be changed, and column temperature can change correspondingly. The column can have a pressure capacity suitable for liquid chromatography such as, for example, 0 to about 1,000 psi, or alternatively, 0 to about 5,000 psi. The column can comprise at least first and second layers of polymer material on each other, wherein the first layer cuts through the second layer. The column can comprise a polymer layer which is anchored to the substrate. These engineering designs can increase the pressure capacity and provide more strength.

Another embodiment of the invention is a chip-based temperature controlled liquid chromatography device comprising a substrate, a thermal isolation zone, and a separation column thermally isolated from the substrate by the thermal isolation zone. In one embodiment, the thermally isolated separation column is on a silicon island, and the silicon island is supported by a structure with a low thermal conductivity. The thermal isolation zone can reduce power consumption and enable the device to have multiple temperature zones.

Another embodiment of the invention is a chip-based liquid chromatography device comprising a temperature sensor that provides a feedback control during operation. In one specific embodiment, a heater can serve as the temperature sensor, and the temperature can be determined by passing current through the heater and monitoring the voltage drop. In another embodiment, the temperature sensor can be integrated on the chip and coupled to the column to provide feedback control.

Another embodiment of the invention is an apparatus for chip-based liquid chromatography comprising a liquid chromatography separation column on a substrate and a cooling device such as, for example, a thermoelectric cooling device for temperature control. A cooling device can be a Peltier device on the substrate and coupled to the column to enable cooling. Alternatively, a cooling device is an off chip Peltier device thermally coupled to the chip.

The invention also provides methods of making a chip-based temperature gradient liquid chromatography device. The method involves forming a liquid chromatography separation column by depositing and patterning a polymer material on a substrate, and forming a heater by depositing and patterning a metal layer. Two types of manufacture process flows, called herein Version I and Version II, are disclosed representing different engineering structures for different needs.

Another embodiment of the invention is a liquid chromatography apparatus comprising a chip-based temperature controlled liquid chromatography device, a fluidic coupling for the device, and an electrical interface.

Finally, the invention provides methods of using chip-based temperature controlled LC separation device comprising controlling temperature by adjusting a power input. Controlling temperature optimizes a liquid chromatography separation. In some embodiments, controlling temperature comprises using a spatial or temporal temperature gradient for a separation.

Advantages of the invention include better, more sophisticated thermal management in liquid chromatographic separations.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 illustrates a Version I device process flow.

FIG. 8 illustrates a Version II device process flow.

DETAILED DESCRIPTION OF THE PREFERRED EMBODIMENTS

The invention provides a variety of embodiments directed to on-chip temperature controlled liquid chromatography, methods of making, and methods of using.

Priority U.S. Provisional Application No. 60/545,727 filed Feb. 17, 2004 (CalTech Ref. No.: CIT-4046P) "On-Chip Temperature Controlled Liquid Chromatography Methods and Devices" is hereby incorporated by reference in its entirety including the figures.

The following related patent applications can be useful for understanding and practicing this invention:

(i) U.S. patent application Ser. No. 10/917,257 (CIT-3936) "IC-processed Polymer Nano-liquid Chromatography System" by Tai et. al. filed Aug. 11, 2004, and claiming the priority to U.S. provisional patent application No. 60/496,964 filed Aug. 20, 2003, which is hereby incorporated by reference in its entirety;

(ii) U.S. patent application Ser. No. 10/391,122 (CIT-3619) "A Method for Integrating Micro- and Nanoparticles Into MEMS and Apparatus Including the Same" by Tai et. al. filed Mar. 18, 2003, and claiming the priority to U.S. provisional patent application No. 60/366,019, filed Mar. 19, 2002, which are all incorporated hereby by reference in their entirety;

(iii) U.S. provisional patent application "Integrated LC-ESI on a Chip" by Tai et. al. No. 60/586,576 (CIT-4151P), filed Jul. 9, 2004, incorporated hereby by reference in its entirety;

(iv) U.S. provisional patent application No. 60/592,588 (CIT-4166P) "Modular Microfluidic Packaging System" by Tai et. al. filed Jul. 28, 2004, incorporated hereby by reference in its entirety.

Also, the following technical literature can be useful for understanding and practicing of the invention: (i) Shih et. al. "On-Chip Temperature Gradient Liquid Chromatography", *IEEE MEMS* 2005, Miami pp. 782-785 incorporated hereby by reference in its entirety; (ii) He et. al. "Ion Liquid Chromatography On-A-Chip with Beads-Packed Parylene Column", *IEEE MEMS* 2004, Maastricht, The Netherlands, pp. 212-215, incorporated hereby by reference in their entirety.

Additional background for use in practicing the invention can be found in, for example, (i) Panagiotopoulos et al., *J. of Chromatography*, vol. 920, 2001, pp. 13-22; (ii) Andersen et al., *J. of Separation Science*, vol. 26, 2003, pp. 1133-1140; (iii). Lee et al., *Polymer*, vol. 40, 1999, pp. 7227-7231; (iv) Chang et al., *American Laboratory*, vol. 34, 2002, pp. 39; (v) Molander et al., *The Analyst*, vol. 128, 2003, pp. 1341-1345, which are hereby incorporated by reference in their entirety; (vi) Madou, *Fundamentals of Microfabrication, The Science of Miniaturization*, $2^{nd}$ Ed., CRC Press, 2002, including descriptions about micromachining and microfluidics; (vii) Kovacs, *Micromachined Transducers SourceBook*, McGraw Hill, 1998 including descriptions about micromaching and microfluidics; and (viii) Koch, Evans, Brunnschweiler, *Microfluidic Technology and Applications*, Research Studies Press, 2000, including description about chromatography.

Heater

Figure 1:
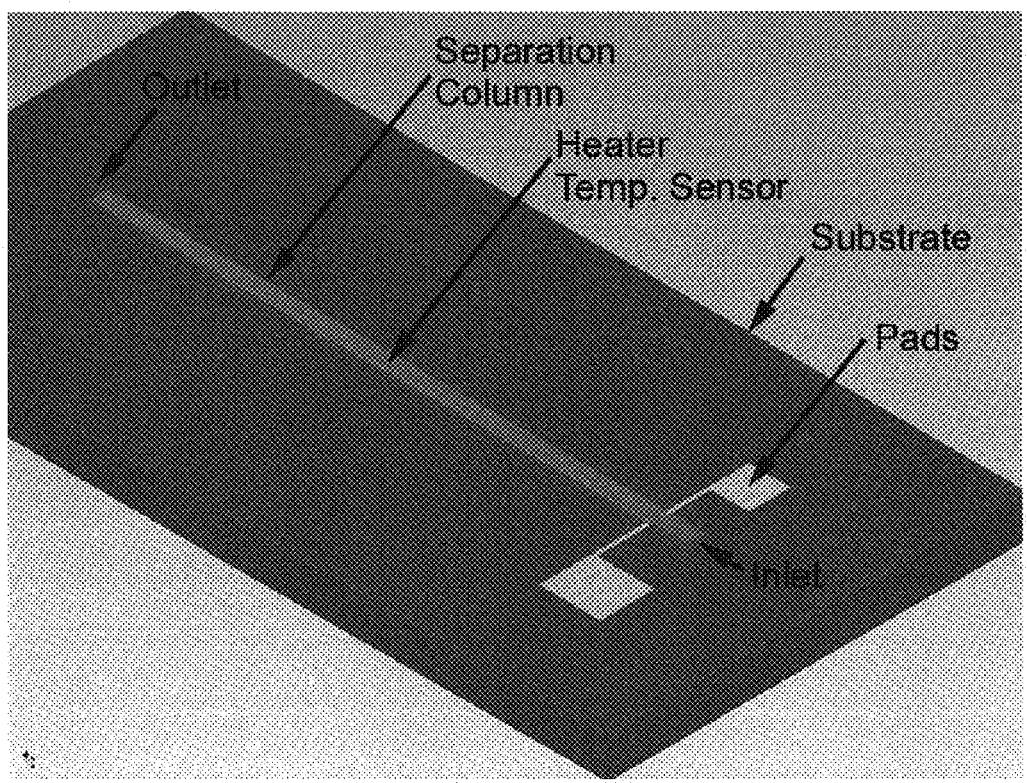
FIG. 1 shows on-chip temperature controlled liquid chromatography separation column.

In one embodiment, the invention provides a separation column on a substrate that is coupled to or integrated with a heater. (FIG. 1) The heater can control column temperature during a separation. When applied current to the heater is changed, column temperature will change correspondingly. The current can be supplied by off-chip electronics or an on-chip integrated circuit. The separation column has an inlet and an outlet to provide fluid access. At least one detector or more can be integrated on the substrate. Precise temperature programming can be achieved by this device.

In a preferred embodiment, the column is packed with beads as a separation bed, such as $C_{18}$ coated fused silica beads for Reverse Phase-HPLC. Packing of particles into microfabricated structures is described in, for example, U.S. patent application Ser. No. 10/391,122 (CIT-3619) by Tai et. al. "A Method for Integrating Micro- and Nanoparticles Into MEMS and Apparatus Including the Same" filed Mar. 18, 2003, and claiming the priority to U.S. provisional patent application No. 60/366,019, filed Mar. 19, 2002, which are incorporated hereby by reference in their entirety. In another preferred embodiment, the column can be formed by micromachining using a polymer, such as, for example, parylene or polyimide, as structural material.

The substrate can be, for example, silicon or glass.

The heater can comprise a number of different materials. In a preferred embodiment, the heater for example is metal, or polysilicon. The heater can be in contact with the column or in vicinity so that heat transfer is efficient and sufficient.

In addition, an on-chip LC device with a heater can achieve substantial pressure capacity. For example, an column inner pressure on such a device could reach up to 5,000 psi. In the examples described herein, devices were able to stand a column inner pressure of at least 600 psi (also called pressure capacity).

Thermal Isolation

Figure 2:
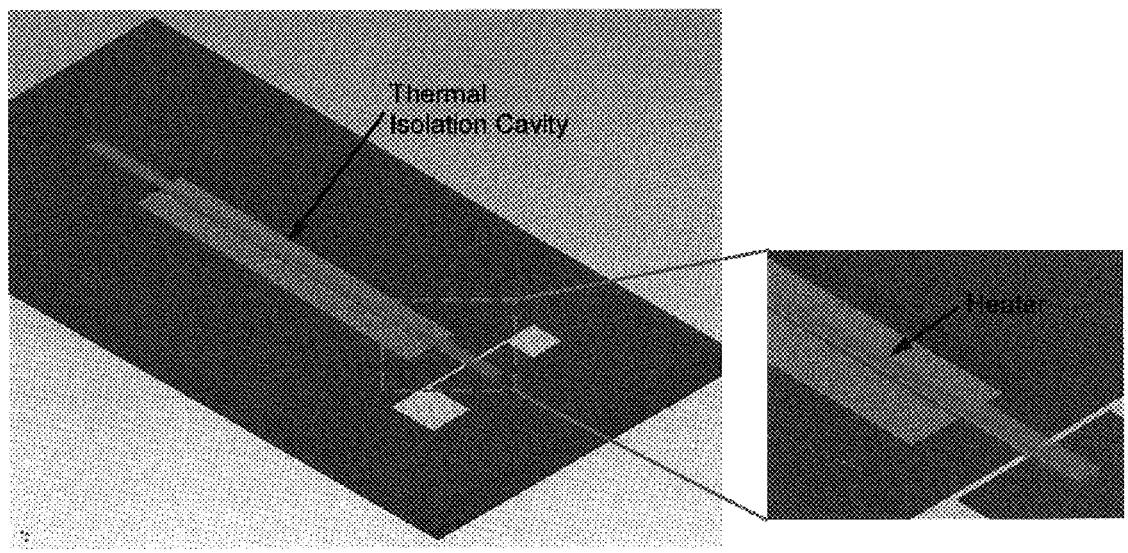
FIG. 2 shows a chip with a surface micromachined thermal isolation cavity/zone. Inlet shows enlarged picture of suspended column and heater.
Figure 3:
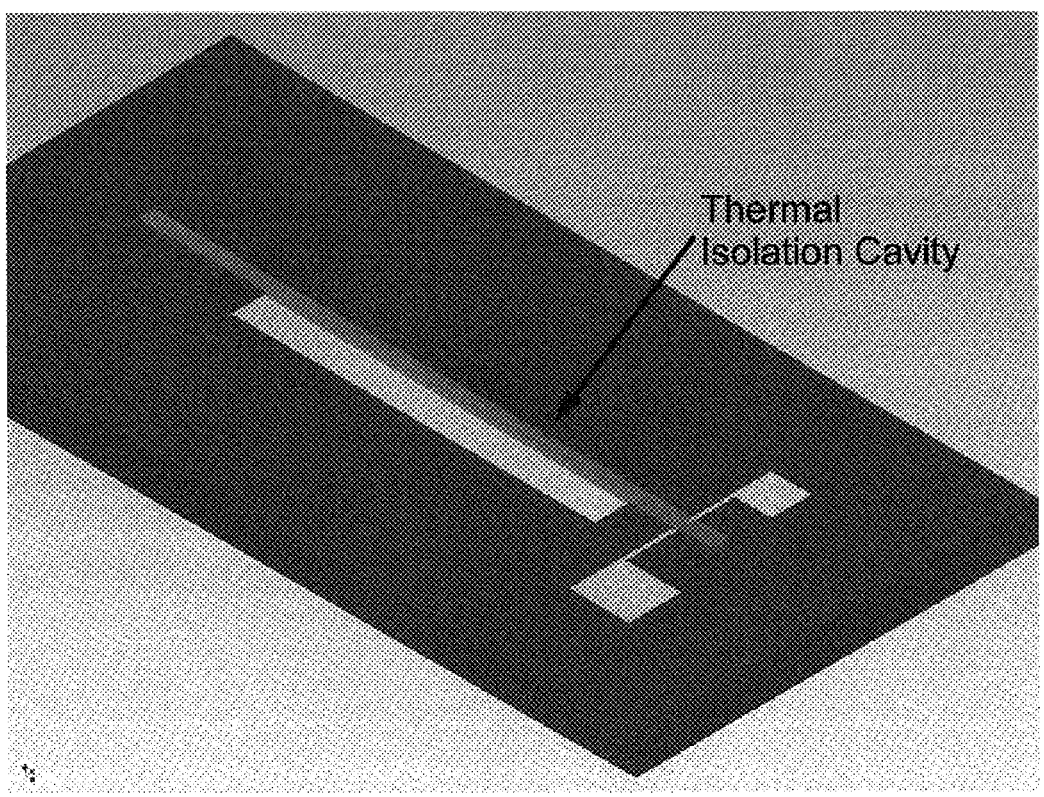
FIG. 3 shows a chip with a bulk micromachined thermal isolation cavity/zone.

Another embodiment of the invention is a chip-based controlled liquid chromatography device comprising a substrate, a thermal isolation zone or cavity, and a separation column thermally isolated from the substrate by the thermal isolation zone or cavity. Terms "thermal isolation zone" and "thermal isolation cavity" are used interchangingly in this application. The thermal isolation zone can be integrated with other device components. The thermal isolation zone allows one to reduce power consumption and enable fast and precise temperature adjustment. FIGS. 2 and 3 show the main part of the column thermally isolated from the substrate by a thermal isolation cavity filled with air and created by bulk or surface micromachining respectively. Alternatively, the thermal isolation cavity can be also filled with a medium with a low thermal conductivity (e.g., less than 1 W/(m·K)), such as oil or a proper polymer. Thermal conductivity of materials is described in, for example, Shackelford, *Introduction to Materials Science for Engineers*, 4th Ed., including pages 327-328. Surface micromachining of the thermal isolation cavity can be performed by $BrF_3$ or $XeF_2$ gas phase etching. Bulk micromachining of the thermal isolation cavity can be accomplished by DRIE or KOH etching. The thermal isolation cavity can be also formed by a combination of surface and bulk micromachining.

Figure 4:
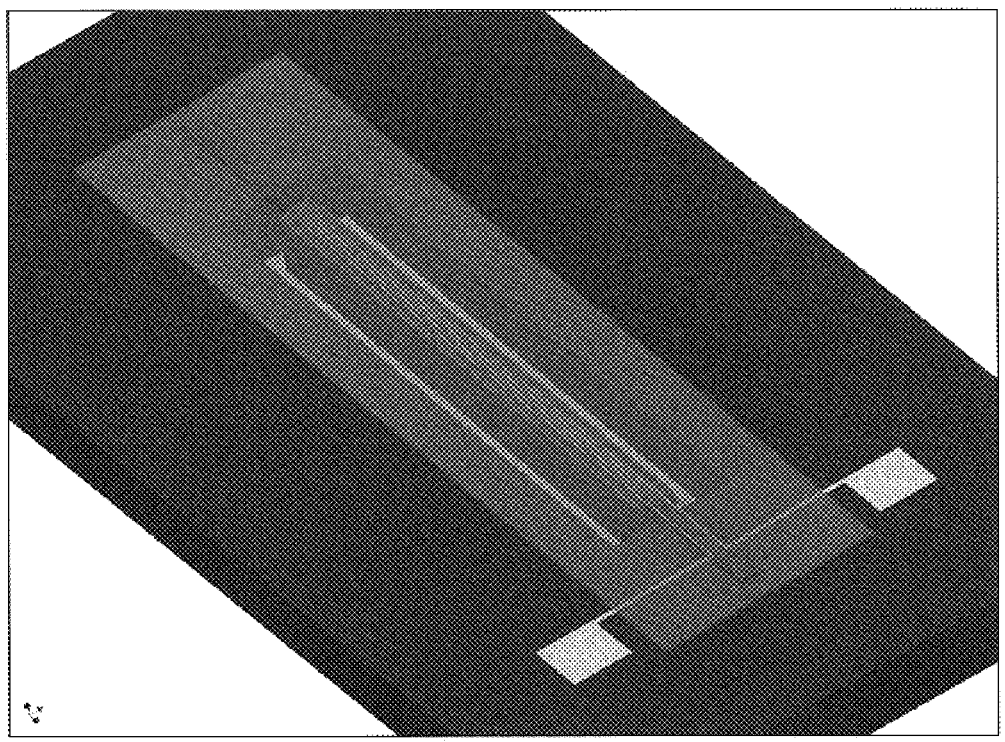
FIG. 4 shows a chip with a silicon island with a thermal isolation cavity.
Figure 9:
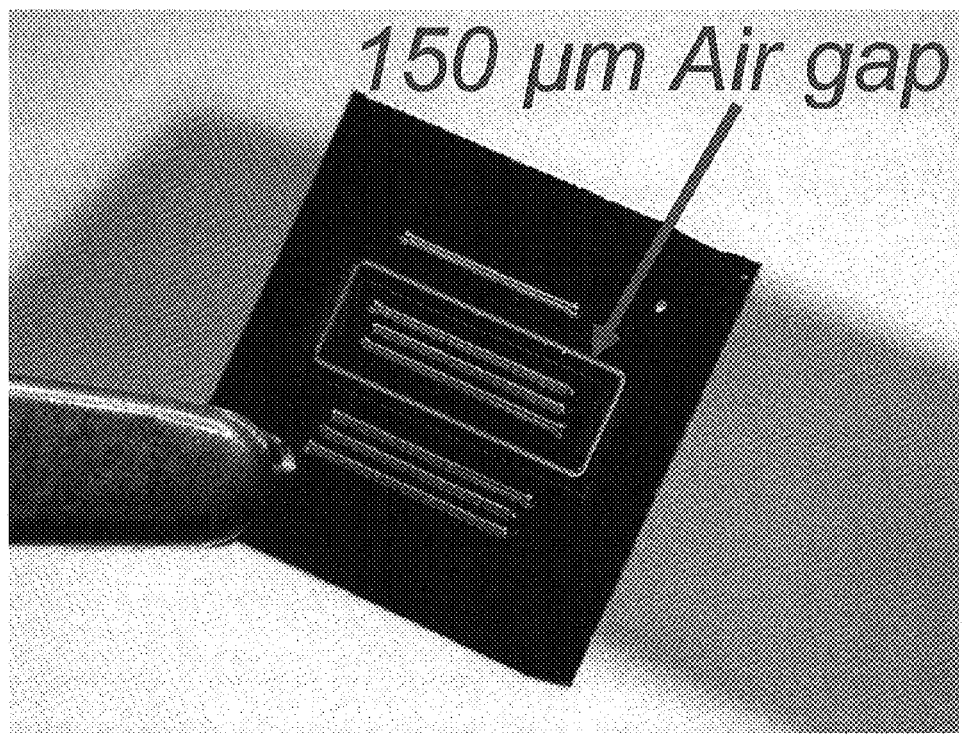
FIG. 9 demonstrates details of a Version II device.

In another embodiment of the invention (FIG. 4), the column is on a silicon island, and the island is supported by a structure with a low thermal conductivity (less than 1 W/(m·K)), such as parylene. The structure can be beams or a membrane. FIG. 9 shows a silicon island surrounded by a 150 μm wide through-wafer air gap.

The thermal isolation cavity can enable multiple temperature zones on the device. For example, the column can be at one first temperature, the detector can be at a second temperature, and the thermal isolation cavity can keep the temperatures different. Fluidic and electrical paths can cross the thermal isolation zone and reach other temperature zones.

Temperature Sensor

In yet another embodiment, the invention is a chip-based temperature controlled liquid chromatography device comprising a temperature sensor that provides feedback control during operation. See, for example, U.S. Pat. No. 6,526,823 for "Microelectromechanical System Sensor Assembly" to Tai et al, which is hereby incorporated by reference in its entirety; see also, U.S. Patent Publication No. 2004/0188648 published Sep. 30, 2004 to Tai et al. "Integrated Surface-Machined Micro Flow Controller Method and Apparatus," also incorporated by reference in its entirety. The sensor can be, for example, an electrochemical sensor. In one embodiment, the heater can serve as the temperature sensor. The temperature on the heater can be determined by passing current through the heater and monitoring the voltage drop. Based on that information, the applied current can be adjusted according to a desired temperature profile. The system can be calibrated to find out a suitable current profile for a given temperature gradient profile and a given flow rate. The use of the on-chip heater as a temperature sensor is described, for example, in E. Meng and Y. C. Tai, *Technical Digest, The* 12th *International Conference on Solid-State Sensors, Actuators and Microsystems Transducers* 2003, Boston, USA, pp. 686-689, incorporated hereby by reference in its entirety. In another embodiment, the temperature sensor can be integrated on the chip and coupled to the column to provide feedback control.

Cooling

Another embodiment of the invention is an apparatus for chip-based liquid chromatography comprising a cooling device. An example of a cooling device is a thermoelectric device. The cooling device can be integrated into the substrate and other device components. A cooling device can be a Peltier device on the substrate and can be coupled to the column to enable cooling. Alternatively, a cooling device can be an off chip Peltier device thermally coupled to the chip.

Versions I and II Devices; Methods of Making

The invention also provides methods of making an on-chip temperature gradient liquid chromatography device. For example, a separation column can be formed by depositing and patterning a polymer material on a substrate, and a heater can be formed by depositing and patterning a metal layer on the column. Two general types of devices, Version I and II are described in further detail although the invention is not limited to these two versions. Different types of devices can be fabricated to satisfy different separation criteria. For example, the important parameter of pressure capacity can be controlled.

Two detailed process flows are provided (FIGS. 5 and 8). In the first process flow (also referred to as a Version I device process flow) illustrated on FIG. 5, an oxide can be grown on the substrate, and the oxide on the front side of the substrate can be patterned. A metal layer can be then deposited on the substrate and patterned. The selection of metal layer composition is not particularly limited. For example, the metal layer can be, for example, Al, Cr, Ti, Au, Pt or a combination of these. Next, the oxide on the backside of the wafer can be patterned, and deep reactive ion etching can be performed on the backside of the wafer.

A layer of polymer material can be then deposited on the front side of the wafer and patterned. In a preferred embodiment, the polymer material can be parylene. A sacrificial layer can be then deposited and patterned on the front side of the wafer. Photoresist is one example of a sacrificial layer. Next, deep reactive ion etching can be performed on the front side of the wafer.

A second layer of polymer material, preferably parylene, can be then deposited and patterned on the front side of the wafer. Deep reactive ion etching can be performed on the backside of the wafer to open through holes. A front side etch can be performed, preferably using $XeF_2$.

Finally, a third layer of polymer material, preferably parylene, can be deposited. After dicing, the sacrificial layer inside the fluidic channel can be released, and the polymer material can be patterned with a shadow masking.

Figure 6:
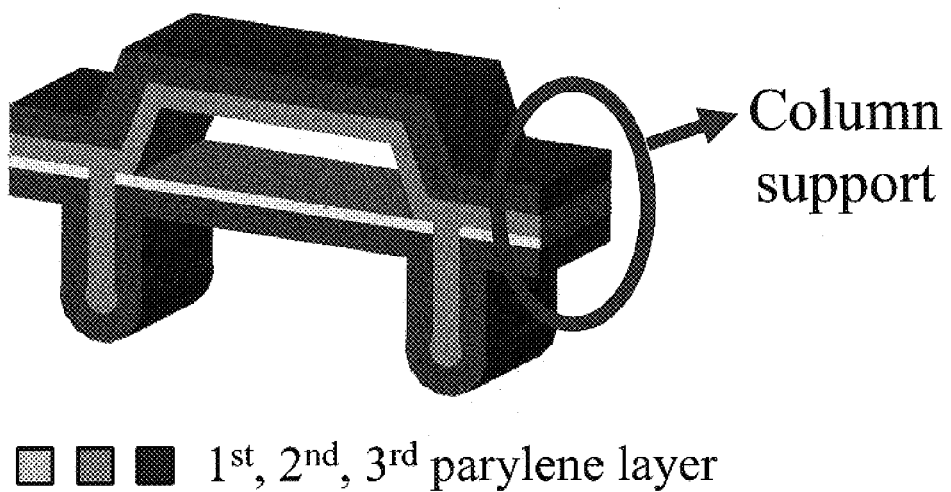
FIG. 6 demonstrates a cross section a Version I device.

Several column structures can be used to achieve a great pressure capacity. As shown in FIG. 6, the second parylene layer can cut through the first parylene layer and avoid liquid penetration through the $1^{st}/2^{nd}$ parylene interface under high pressure. The pressure capacity of this design can go up to, for example, 180 psi. The incoming liquid can be heated up to equilibrium temperature within 500 μm column length with a regular linear flow velocity (~1 mm/sec).

Figure 7:
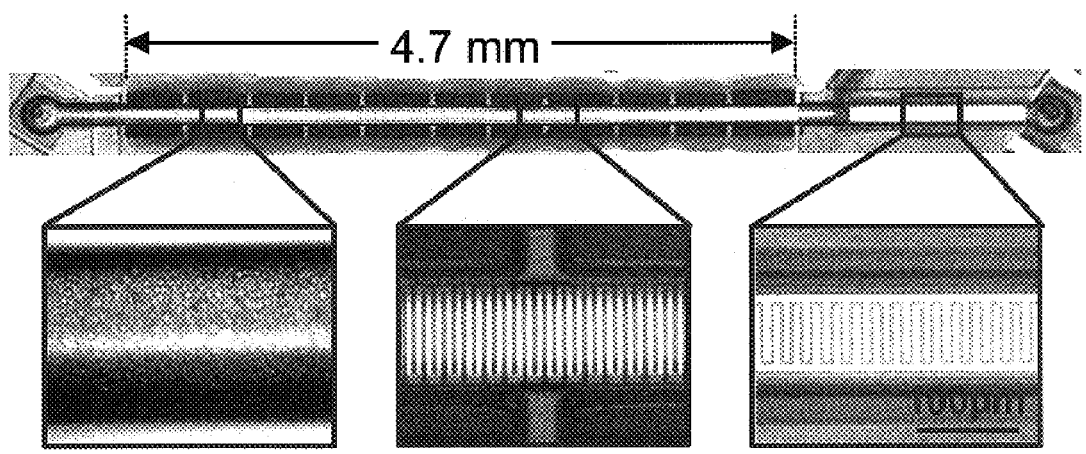
FIG. 7 shows details of a Version I device.

FIG. 7 demonstrates the device made according to this method. Left inlet shows a column after packing with 5 μm silica beads, central inlet presents freestanding column with built-in heater and column supports, and right inlet is an integrated electrochemical sensor.

A second process flow (also referred to as a Version II device process flow) is shown in FIG. 8. A polymer column can be anchored down to the silicon substrate with an integrated electrochemical sensor and distributed heater.

First, an oxide can be grown on the substrate, and a metal film can be then deposited and patterned by a liftoff process on the front side of the wafer. Next, the front side oxide can be patterned, then the oxide on the backside of the wafer can be patterned, and deep reactive ion etching can be performed on the backside of the wafer.

Second, a sacrificial layer, preferably photoresist, can be deposited and patterned on the front side of the wafer, and deep reactive ion etching can be performed on the front side of the wafer.

Third, a polymer material, such as parylene, can be deposited and patterned on the front side of the wafer.

Fourth, a deep reactive ion etching can be performed on the backside of the wafer to open through holes. After dicing, the sacrificial layer inside fluidic channel can be released.

Figure 10:
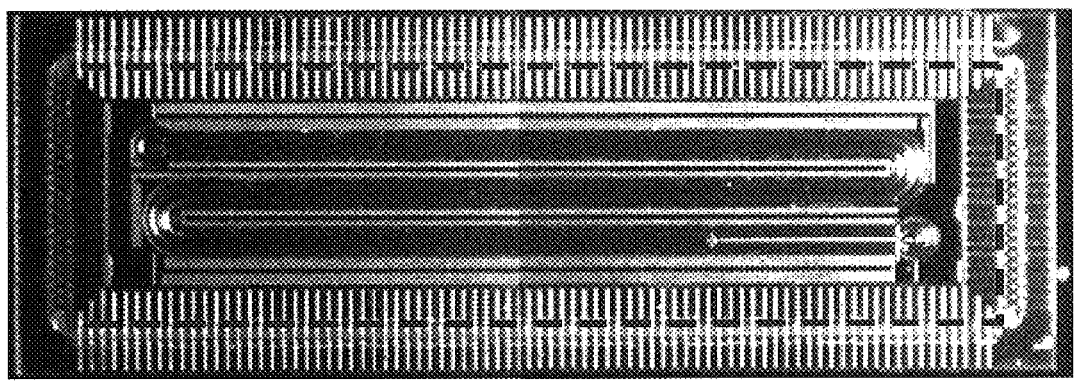
FIG. 10 is a Version II device close-up.

This anchored column structure has been shown to stand a column inner pressure of at least 600 psi (Q. He, et. al., *IEEE MEMS* 2004, Maastricht, The Netherlands, pp. 212-215). In order to stand the jig-clamping and wire-bonding stress during system preparation, chip integrity can be enhanced by the cross-gap parylene membrane and parylene stitches structure. FIG. 9, for example, shows a Version II device with 150 μm wide through-wafer air gap and silicon island (center piece). FIG. 10 shows a Version II device close-up: dashed rectangle defines the silicon island area which is surrounded by the air gap; thin white lines are parylene stitches which cross-link silicon island to the rest of the chip; and running between the HPLC column is the distributed heater.

Pressure capacity is generally sufficiently high to at a minimum allow for liquid chromatography and can be, for example, 0 to about 1,000 psi or, alternatively, 0 to about 5,000 psi. Additional suitable ranges for pressure capacity include, for example, about 100 psi to about 500 psi, or about 500 psi to about 1,000 psi, or about 1,000 psi to about 2,500 psi, or about 2,500 psi to about 5,000 psi. Another suitable range is that sufficient to provide for liquid chromatography to about 180 psi. Another suitable range is that sufficient to provide for liquid chromatography to about 600 psi. One can select the desired pressure capacity and engineer the device accordingly, balancing other factors such as cost and the type of thermal management need.

Packaged Temperature Gradient HPLC System

Figure 13:
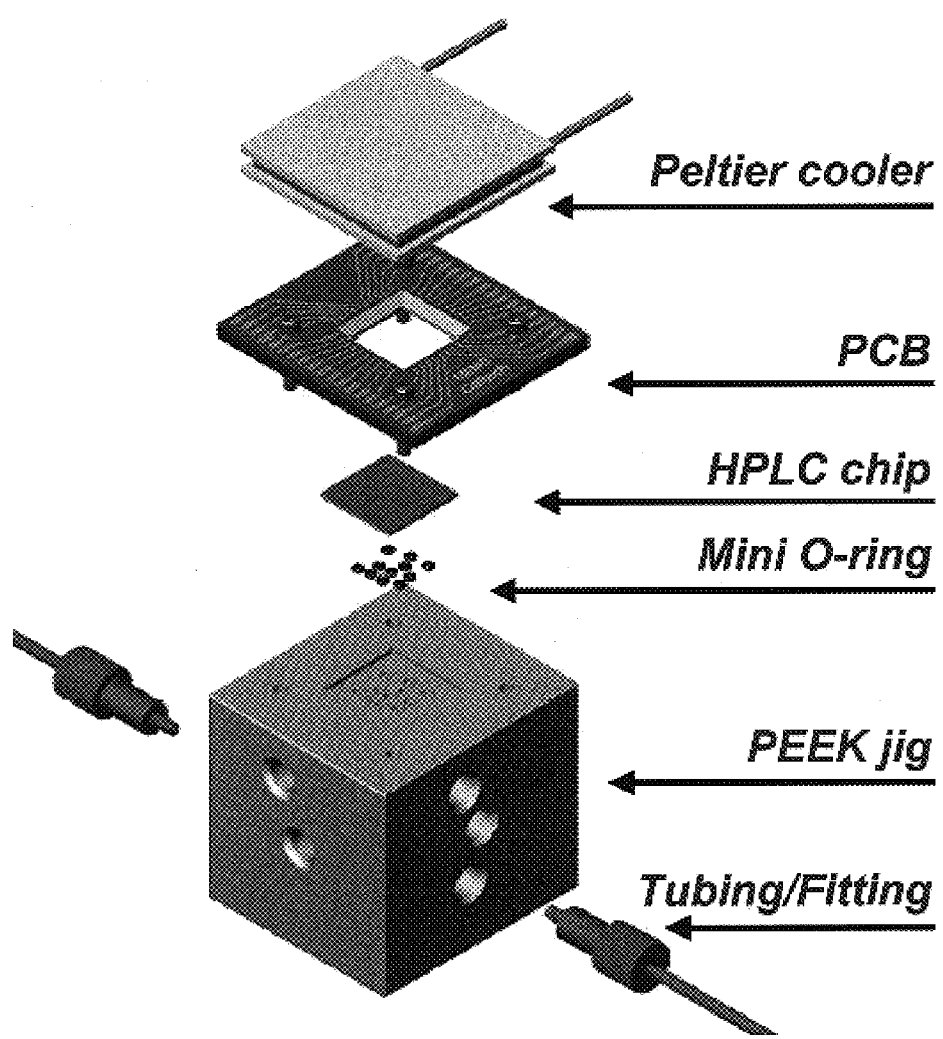
FIG. 13 shows testing packaging for temperature gradient HPLC system.

The invention also provides a packaged temperature gradient HPLC system. FIG. 13 shows one embodiment of the system. The jig can be made of plastic, such as PEEK material or similar plastic materials, which has strong chemical resistance and can be machined easily. Fluid tubing and fitting can plug into the apparatus through openings on the PEEK jig. O-rings with an outer diameter of 1.5 mm can be used to provide a leak-proof interface between the jig and HPLC chip. PCB can be used to clamp down the chip against the O-rings and also provide electrical connection to the chip via wire-bonding. A cooling device, such as a thermoelectric device, such as a Peltier cooler, can be placed on top of PCB when chip cooling is necessary. The present invention can function as a part of a microfluidic packaging system described in U.S. provisional patent application No. 60/592,588 (CIT 4166P) "Modular Microfluidic Packaging System" by Tai et. al. filed Jul. 28, 2004, incorporated hereby by reference in its entirety.

Using On-Chip Temperature Gradient LC System

Figure 15:
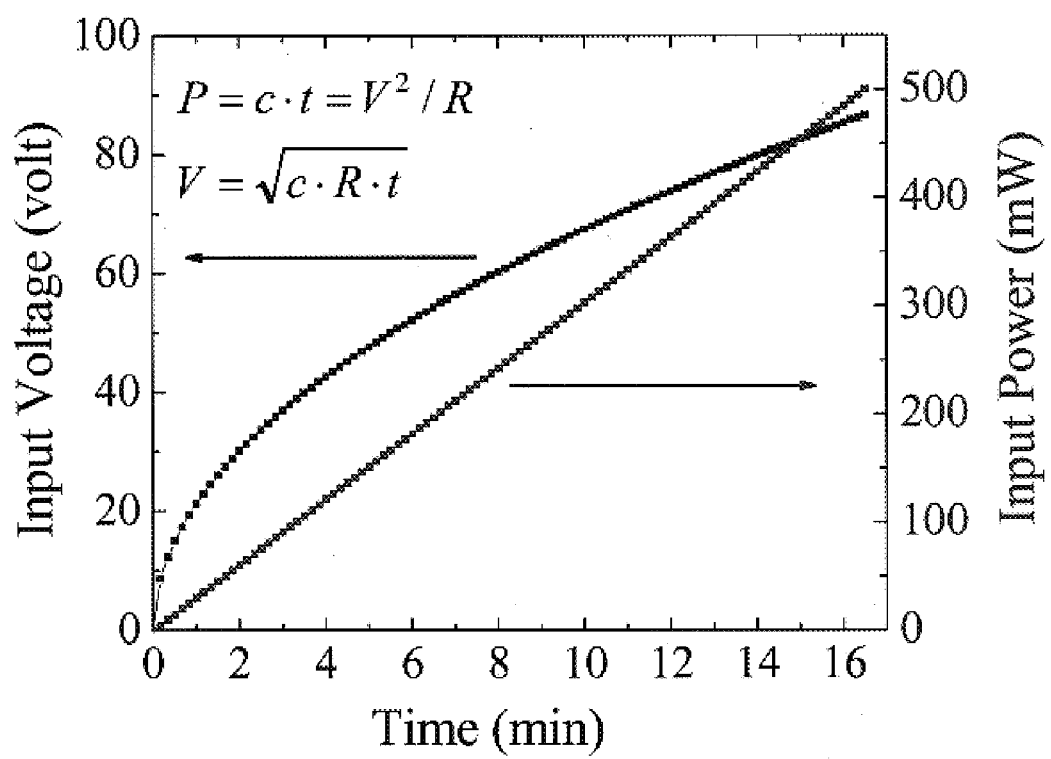
FIG. 15 shows power and voltage input profiles for generation of on-chip constant temperature gradient.

The invention also provides methods of using the temperature gradient to optimize the separation. The temperature gradient can be temporal or spatial. For basic temperature gradient liquid chromatography operation, a constant temperature gradient can be used. FIG. 15, for example, shows a power input to the chip increasing linearly with time. Separations can be performed using fixed column temperature and solvent gradient elution. For some separations that are very sensitive to temperature effect, but not to solvent change, the separations can be based on temperature gradient and isocratic elution. For the most difficult separations, combinations of temperature gradient and solvent gradient can be used.

Applications

The present invention can be used to perform different types of liquid chromatography such as reverse-phase chromatography, normal phase chromatography, size-exclusion chromatography, ion-exchange chromatography, and affinity chromatography.

The potential applications of the invention include, but are not limited to, monitoring and recording a broad spectrum of target analytes. For example, the invention can be utilized to analyze water in the ocean, rivers, aqueducts, or households. The invention can also be used for monitoring food quality and for analysis of bodily fluids, including but not limited to, urine, blood, and saliva.

The invention is further described via non-limiting working examples (see, for example, FIGS. 9, 10, 11, 12, 14, 15, 16, and 17, including several simulations.

EXAMPLE

Power Consumption of Version I and Version II Devices

Figure 14:
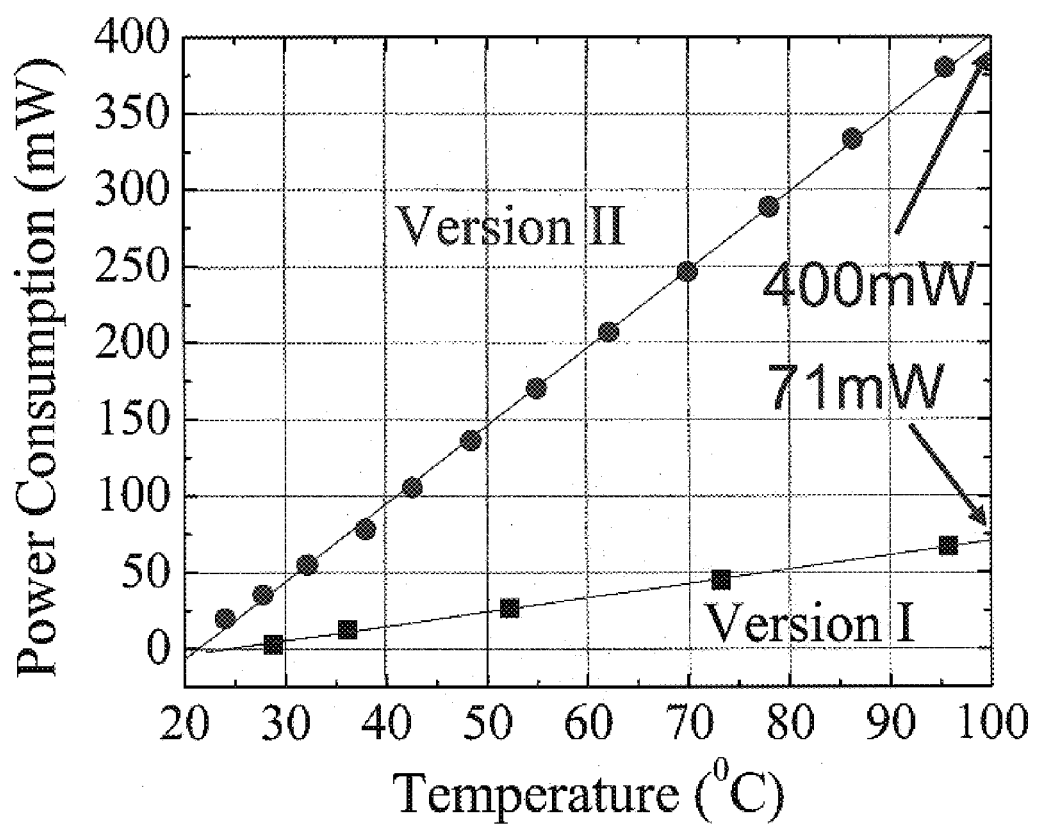
FIG. 14 presents temperature dependencies of power consumption for Version I and Version II devices.

FIG. 14 presents power consumption as a function of temperature for Version I and Version II devices incorporated into a temperature gradient HPLC system. The Version I device has a much lower power consumption due to its smaller heating area exposed to the air.

EXAMPLE

Testing a Performance of a Version II Separation Column Under Stress

Figure 11:
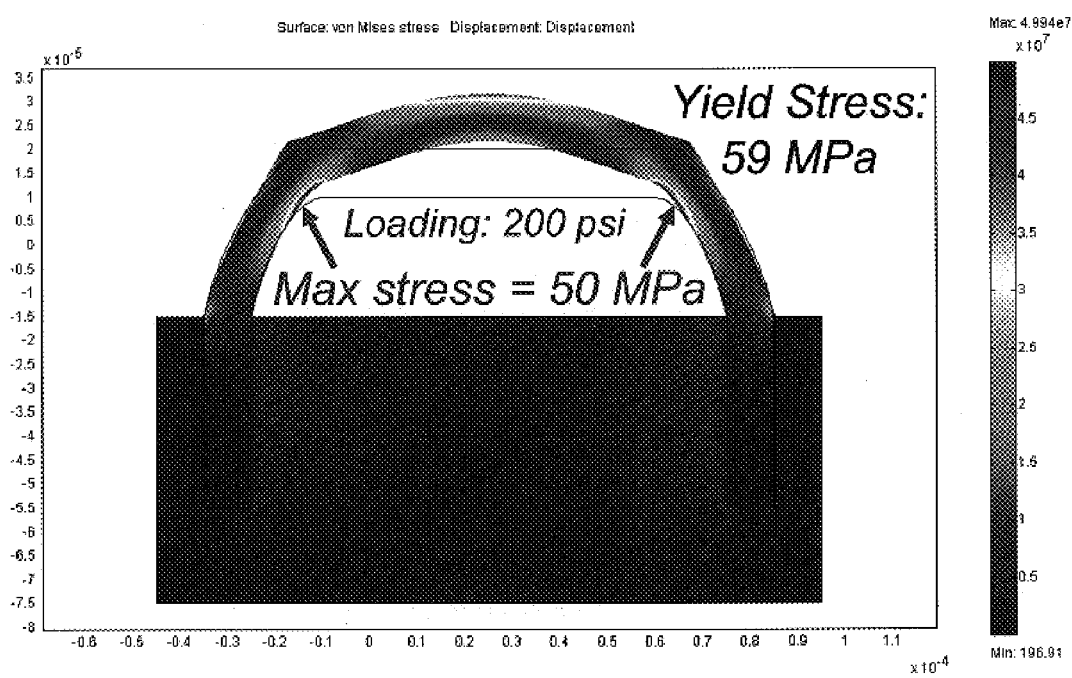
FIG. 11 shows stress distribution in a Version II device.
Figure 12:
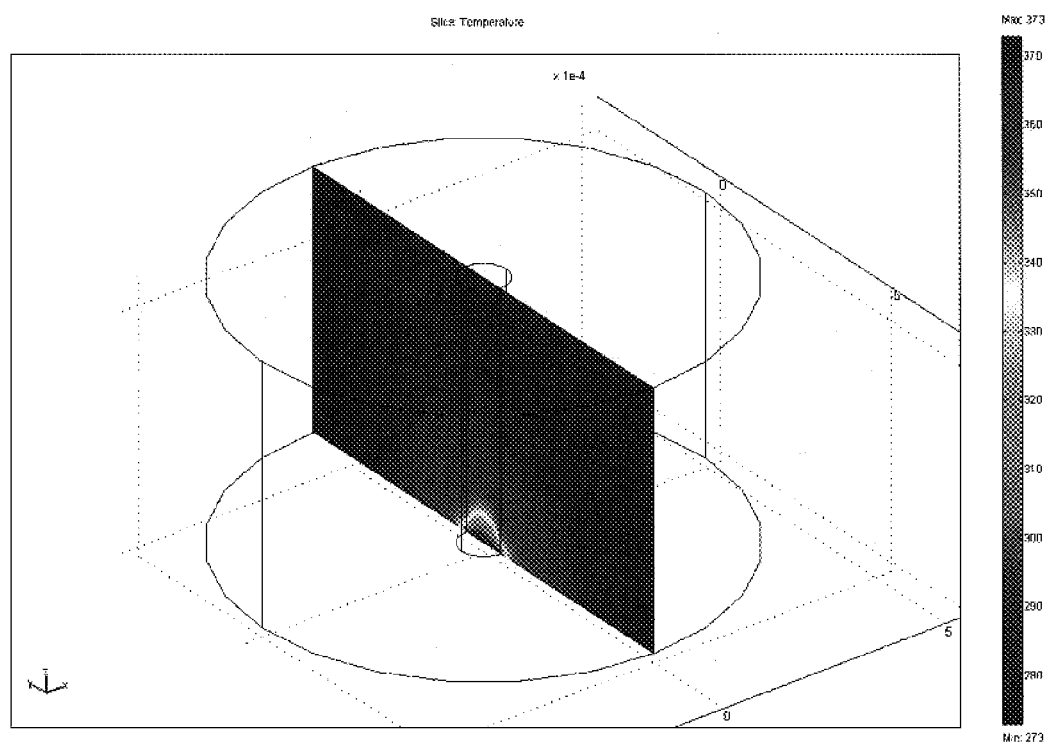
FIG. 12 shows a solvent preheating simulation around the liquid access channel of a Version II device.

To make sure the 10 μm parylene column wall of can stand high pressure without yielding or breaking, the stress distribution was studied in the parylene film under a 200 psi uniform pressure loading in column with FEMLAB modeling package (FIG. 11). The maximum stress happens around the corner of column inner surface and is 50 MPa which is smaller than the parylene yield stress of 59 MPa (C. Y. Shih et. al., *Microsystem Technologies*, 10(5), 407-411, 2004). This indicates that parylene column wall will not have noticeable plastic deformation when operated under 200 psi.

EXAMPLE

Mobile Phase Solvent Preheating in a Version II Separation Column

One important factor for quality temperature gradient liquid chromatography is mobile phase solvent preheating. In other words, mobile phase solvent should be heated up to the desired temperature before it enters the HPLC column. Based on FEMLAB simulation result (FIG. 12), it was found that water-based solvent is heated up to the equilibrium temperature through thermal conduction (within the flow rate range of the invention) inside the liquid access channel before it enters the HPLC column. Therefore, solvent preheating is achieved using devices fabricated according to the process flow of FIG. 8. The simulations were performed using linear flow velocity 4.242 mm/sec and equilibrium temperature 100° C.

EXAMPLE

Testing a Separation Performance of the Temperature Gradient HPLC

Figure 16:
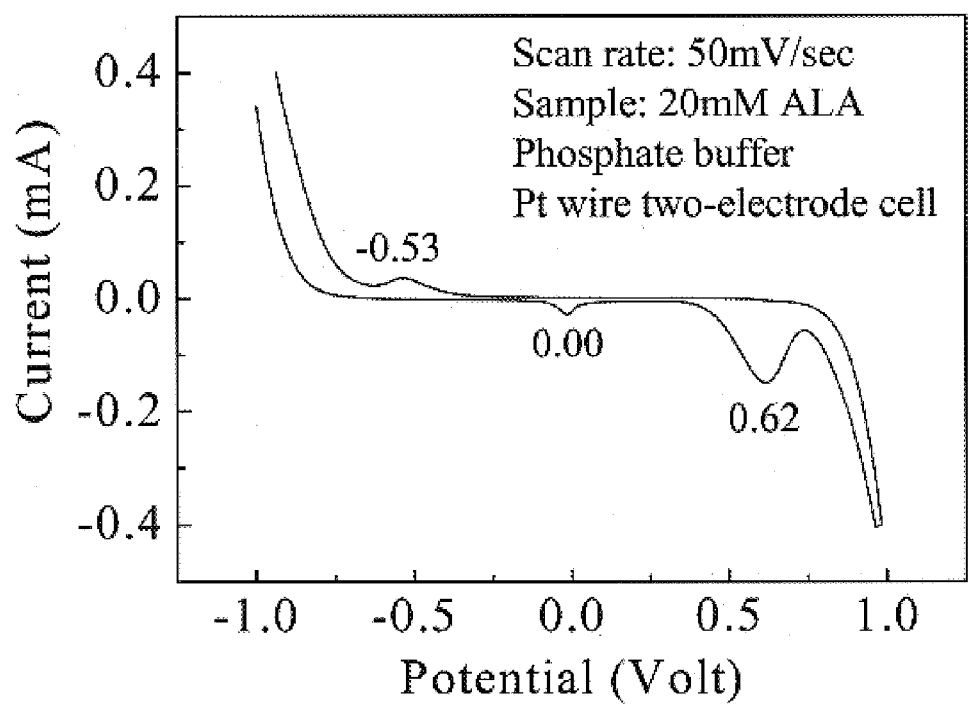
FIG. 16 demonstrates a typical cyclic voltametry of derivatized amino acid at 23° C.

To test the separation performance of the temperature gradient HPLC system, a sample of mixed amino acids was separated. The amino acid sample was first derivatized to become electroactive (B. W. Boyd et. al, *Analytical Chemistry*, 72(4), 865-871). The cyclic voltammetry (CV) of derivatized amino acids was then carried out. FIG. 16 shows a typical CV of derivatized amino acids where peak current potential can be determined and used as the electrochemical sensing potential.

Figure 17:
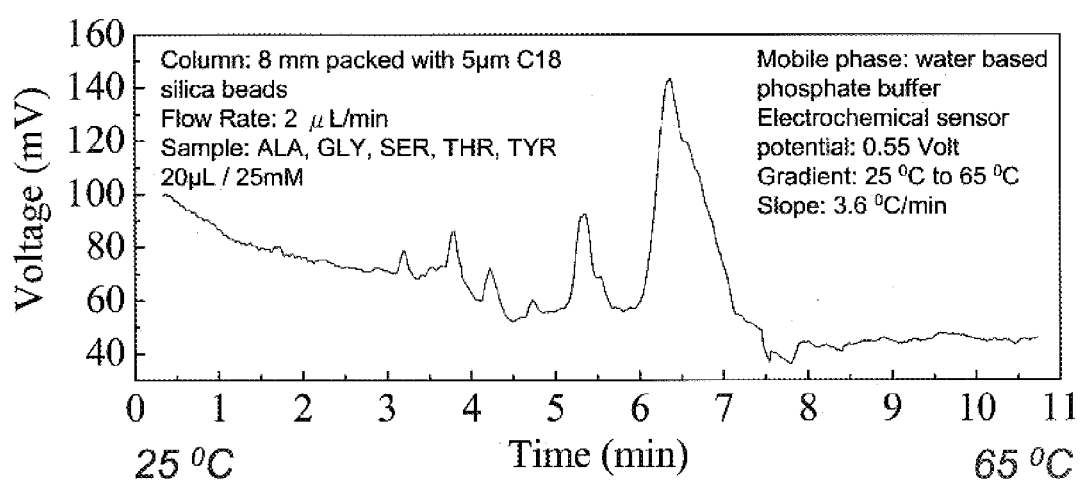
FIG. 17 shows temperature gradient chromatogram of derivatized amino acids obtained using Version II HPLC system.

Version II devices were used for this amino acid separation test. Water-based phosphate buffer with a pH value of 6.5 and a flow rate of 2 μL/min was used as the separation mobile phase. Column temperature ramped up from 25 C to 65 C (while voltage source output from 0 V to 64 V) with a slope of 3.6 C/min during the separation test. FIG. 17 shows the successful on-chip temperature gradient separation and detection of amino acids. To obtain chromatogram of FIG. 17, sample loading was done by flushing the column with 25 mM derivatized amino acids in phosphate buffer at 2 μL/min for 10 min. Column was then flushed with pure phosphate buffer for 10 min before applying temperature gradient. The on-chip temperature gradient separation and detection of amino acids was demonstrated.

All references cited herein are incorporated by reference in their entirety.

What is claimed is:

1. An apparatus for liquid chromatography comprising a liquid chromatography separation column on a substrate, wherein the column is coupled to a heater on the substrate, wherein the substrate is silicon.

2. The apparatus of claim 1, wherein the heater is a metal heater or a polysilicon heater.

3. The apparatus of claim 1, wherein the column comprises a polymer material.

4. The apparatus of claim 1, wherein the column has a pressure capacity of 0 to about 1,000 psi.

5. The apparatus of claim 1, wherein the column has a pressure capacity of 0 to about 5,000 psi.

6. The apparatus of claim 1, wherein the column comprises at least first and second layers of polymer material on each other and the first layer cuts through the second layer.

7. The apparatus according to claim 1, wherein the column comprise a polymer layer which is anchored to the substrate.

8. The apparatus of claim 1, wherein the heater is a temperature sensor.

9. The apparatus of claim 1, further comprising a temperature sensor on the substrate.

10. The apparatus of claim 1, wherein the heater is a metal or polysilicon heater, wherein the column comprises a polymer material, and wherein the heater is a temperature sensor.

11. An apparatus for liquid chromatography comprising a liquid chromatography separation column on a substrate, wherein the column is coupled to a heater on the substrate, wherein the column comprises parylene.

12. A method of making a chip-based temperature gradient liquid chromatography device comprising:
    forming a liquid chromatography separation column by depositing and patterning a polymer material on a substrate; and
    forming a heater on the substrate by depositing and patterning a metal layer.

13. The method of claim 12, wherein the polymer material is parylene.

14. The method of claim 12, wherein the metal layer comprises Al, Cr, Ti, Au, Pt, or a combination thereof.

15. The method of claim 12, further comprising forming a thermal isolation zone on the substrate by bulk micromachining, surface micromachining or a combination thereof, wherein the thermal isolation zone thermally isolates the substrate and the liquid chromatography separation column.

16. An apparatus for liquid chromatography comprising a liquid chromatography separation colunm on a substrate, wherein the colunm is coupled to a heater on the substrate, wherein the substrate is silicon or glass.

* * * * *